United States Patent [19]

Pallos

[11] 4,347,380
[45] Aug. 31, 1982

[54] N-ACYLSULFONAMIDE HERBICIDAL ANTIDOTES

[75] Inventor: Ferenc M. Pallos, Walnut Creek, Calif.

[73] Assignee: Stauffer Chemical Company, Westport, Conn.

[21] Appl. No.: 208,912

[22] Filed: Nov. 21, 1980

Related U.S. Application Data

[62] Division of Ser. No. 31,906, Apr. 20, 1979, Pat. No. 4,266,078.

[51] Int. Cl.³ .......................................... C07C 143/82
[52] U.S. Cl. ................................................. 564/91
[58] Field of Search .......................................... 564/91

[56] References Cited

U.S. PATENT DOCUMENTS

| | | | |
|---|---|---|---|
| 2,901,475 | 8/1959 | Rudner et al. | 564/91 |
| 3,041,374 | 6/1962 | Gregory | 564/91 |
| 3,694,504 | 9/1972 | Danilewicz et al. | 564/91 |
| 3,917,692 | 11/1975 | Grunwald | 564/91 |
| 4,157,257 | 6/1979 | Takematsu et al. | 564/91 |
| 4,266,078 | 5/1981 | Pallos | 564/91 |

FOREIGN PATENT DOCUMENTS

| | | | |
|---|---|---|---|
| 539403 | 11/1931 | Fed. Rep. of Germany | 564/91 |
| 620778 | 3/1949 | United Kingdom | 564/91 |
| 692651 | 6/1953 | United Kingdom | 564/91 |
| 502877 | 6/1976 | U.S.S.R. | 564/91 |
| 562551 | 9/1977 | U.S.S.R. | 564/91 |

*Primary Examiner*—Paul M. Coughlan, Jr.

*Attorney, Agent, or Firm*—Harry A. Pacini

[57] ABSTRACT

Described herein are herbicidal compositions comprised of a thiocarbamate or haloacetanilide herbicide and an antidotally effective amount of an N-acylsulfonamide compound corresponding to the formula

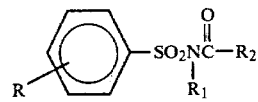

in which
R is selected from the group consisting of hydrogen, methyl, chloro, acetamido, and 1-4 carbon alkoxyamido;
$R_1$ is selected from the group consisting of hydrogen, allyl, and metal ion;
$R_2$ is selected from the group consisting of 1-10 carbon alkyl, 1-4 carbon haloalkyl, 2-4 carbon alkenyl, 2-4 carbon haloalkenyl, acetonyl, 1-6 carbon alkoxy, 1-4 carbon alkoxycarbonyl, 1-4 carbon alkylthioalkyl, alkoxyalkyl, O,O-dialkylphosphorodithioylalkyl, phenyl, halophenyl, halophenylthioalkyl, cyclohexanedione, and dimethyl barbituric acid; or
$R_1$ and $R_2$ together with the carbonyl group to which $R_2$ is attached are selected from the group consisting of succinimide, substituted succinimide, phthalimide, and substituted phthalimide.

3 Claims, No Drawings

N-ACYLSULFONAMIDE HERBICIDAL ANTIDOTES

This is a division, of application Ser. No. 31,906, filed Apr. 20, 1979, Pat. No. 4,266,078.

BACKGROUND OF THE INVENTION

Uses of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control increases crop yield and reduces harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre, usually from 0.1 to 25 pounds per acre. The actual amount used depends upon several considerations including particular weed susceptibility and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. Nos. 4,021,224 and 4,021,229 and Belgian Pat. No. 846,894.

Although several explanatory theories have been advanced, the precise mechanism by which an antidote reduces herbicidal injury has not been empirically verified. An antidote compound may in fact be a remedy, interferent, protectant, or antagonist. As used herein "antidote" describes the effect of herbicidal phytotoxicity to weed species and reduced or non-phytotoxicity to cultivated crop species.

PRIOR ART

Thiocarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Haloacetanilide herbicides have a similar utility. Frequently, the beneficial use of either herbicide requires the addition of an antidotal compound.

U.S. Pat. No. 4,021,229 describes herbicidal compositions consisting of a thiocarbamate herbicide and a sulfonamide antidote. These compositions are particularly effective for the reduction of injury to corn without sacrificing herbicidal effectiveness.

DESCRIPTION OF THE INVENTION

It has been discovered that acylsulfonamide compounds are particularly effective as antidotes for the protection of soybeans from thiocarbamate herbicidal injury. Acylsulfonamide compounds have the following formula

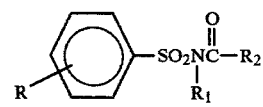

in which

R is selected from the group consisting of hydrogen, methyl, chloro, acetamido, and 1–4 carbon alkoxyamido;

$R_1$ is selected from the group consisting of hydrogen, allyl, and metal ion;

$R_2$ is selected from the group consisting of 1–10 carbon alkyl, 1–4 carbon haloalkyl, 2–4 carbon alkenyl, 2–4 carbon haloalkenyl, acetonyl, 1–6 carbon alkoxy, 1–4 carbon alkoxycarbonyl, 1–4 carbon alkylthioalkyl, alkoxyalkyl, O,O-dialkylphosphorodithioylalkyl, phenyl, halophenyl; halophenylthioalkyl, cyclohexanedione, and dimethyl barbituric acid; or $R_1$ and $R_2$ together with the carbonyl group to which $R_2$ is attached are selected from the group consisting of succinimide, substituted succinimide, phthalimide, and substituted phthalimide.

The present invention includes a two-part herbicidal system comprised of (a) an antidotally effective amount of an N-acylsulfonamide compound of the formula

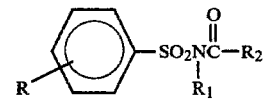

in which

R is selected from the group consisting of hydrogen, methyl, chloro, acetamido, and 1–4 carbon alkoxyamido;

$R_1$ is selected from the group consisting of hydrogen, allyl, and metal ion;

$R_2$ is selected from the group consisting of 1–10 carbon alkyl, 1–4 carbon haloalkyl, 2–4 carbon alkenyl, 2–4 carbon haloalkenyl, acetonyl, 1–6 carbon alkoxy, 1–4 carbon alkoxy carbonyl, 1–4 carbon alkylthioalkyl, alkoxyalkyl, O,O-dialkylphosphorodithioylalkyl, phenyl, halophenyl, halophenylthioalkyl, cyclohexanedione and dimethyl barbituric acid; or $R_1$ and $R_2$ together with the carbonyl group to which $R_2$ is attached are selected from the group consisting of succinimide, substituted succinimide, phthalimide, and substituted phthalimide; and (b) an herbicidally effective amount of a thiocarbamate of the formula

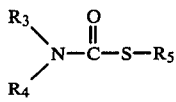

in which

R₃ is selected from the group consisting of 1-6 carbon alkyl and 2-6 carbon alkenyl;

R₄ is selected from the group consisting of 1-6 carbon alkyl, 2-6 carbon alkenyl, cyclohexyl and phenyl; or R₃ and R₄ taken together with the nitrogen atom to which they are attached form an alkylene ring; and R₅ is selected from the group consisting of 1-6 carbon alkyl, 1-6 carbon haloalkyl, 5-10 carbon alkylene ring, phenyl, substituted phenyl, benzyl and substituted benzyl.

The present invention also includes a two-part herbicidal system comprised of (a) an antidotally effective amount of an N-acylsulfonamide compound of the formula

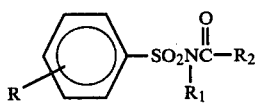

in which

R is selected from the group consisting of hydrogen, methyl, chloro, acetamido, and 1-4 carbon alkoxyamido;

R₁ is selected from the group consisting of hydrogen, allyl, and metal ion;

R₂ is selected from the group consisting of 1-10 carbon alkyl, 1-4 carbon haloalkyl, 2-4 carbon alkenyl, 2-4 carbon haloalkenyl, acetonyl, 1-6 carbon alkoxy, 1-4 carbon alkoxy carbonyl, 1-4 carbon alkylthioalkyl, alkoxyalkyl, O,O-dialkylphosphorodithioylalkyl, phenyl, halophenyl, halophenylthioalkyl, cyclohexanedione and dimethyl barbituric acid; or R₁ and R₂ together with the carbonyl group to which R₂ is attached are selected from the group consisting of succinimide, substituted succinimide, phthalimide, and substituted phthalimide; and (b) an herbicidally effective amount of an haloacetanilide of the formula

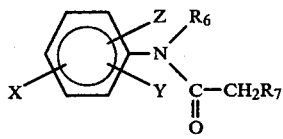

in which

X, Y, and Z are independently selected from the group consisting of hydrogen and 1-4 carbon alkyl;

R₆ is selected from the group consisting of 1-6 carbon alkyl, 2-10 carbon alkylalkoxy, 2-6 carbon acetoxy, and dioxane; and R₇ is selected from the group consisting of chlorine, bromine and iodine.

The terms "alkyl," and "alkenyl," as used herein are intended to include both straight- and branched-chain groups. All carbon atom ranges are intended to be inclusive of both upper and lower limits.

This invention also includes the method of protecting crops from thiocarbamate herbicidal injury which comprises applying to the locus where protection is desired an antidotally effective amount of an N-acylsulfonamide compound of the formula

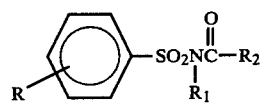

in which

R is selected from the group consisting of hydrogen, methyl, chloro, acetamido, and 1-4 carbon alkoxyamido;

R₁ is selected from the group consisting of hydrogen, allyl, and metal ion;

R₂ is selected from the group consisting of 1-10 carbon alkyl, 1-4 carbon haloalkyl, 2-4 carbon alkenyl, 2-4 carbon haloalkenyl, acetonyl, 1-6 carbon alkoxy, 1-4 carbon alkoxy carbonyl, 1-4 carbon alkylthioalkyl, alkoxyalkyl, O,O-dialkylphosphorodithioylalkyl, phenyl, halophenyl, halophenylthioalkyl, cyclohexanedione and dimethyl barbituric acid; or R₁ and R₂ together with the carbonyl group to which R₂ is attached are selected from the group consisting of succinimide, substituted succinimide, phthalimide, and substituted phthalimide.

Preparation

The thiocarbamates of the present compositions can be prepared by the procedures described in the commonly assigned and expired U.S. Pat. Nos. 2,913,324 and 3,185,720. The haloacetanilide can be prepared by the procedures described in U.S. Pat. No. 3,442,945.

The acylsulfonamide compounds of this invention represented by the above formula can be prepared by several different procedures depending upon the starting materials. The following procedures are general methods of preparation.

A large excess of a sulfonamide is reacted with an aliphatic acid chloride. The mixture is allowed to cool. A precipitate usually forms immediately. If the precipitate does not form, it can be produced by stirring the mixture with pentane. The product N-aliphatic acylsulfonamide is recovered by filtration and thoroughly washed with pentane.

N-aromatic acylsulfonamides can be prepared by refluxing a sulfonamide and the molar equivalent of an aromatic acid chloride in phosphorusoxychloride. The product is allowed to cool and recovered by filtration.

The following are examples of the preparation of specific compounds which appear in Table I.

EXAMPLE 1

(Compound No. 12)

Preparation of N-2-chloropropionyl-O-toluene sulfonamide

O-toluenesulfonamide (10.0 grams (g)) and 20.0 milliliters (ml) of 2-chloropropionylchloride were refluxed for 4 hours. The mixture was cooled and the crystalline solid was filtered. The filtrate was stirred with pentane for one hour and filtered. The product was washed with pentane and dried.

The product consisted of 14.3 g of N-2-chloropropionyl-O-toluene sulfonamide (m.p. 99°–100° C.). Structure was confirmed by infrared (IR) and nuclear magnetic resonance (NMR).

EXAMPLE 2

(Compound No. 26)

Preparation of N-(4-chlorophenylthioacetyl) 4'-chlorobenzene sulfonamide

The reactant N-chloroacetyl 4-chlorobenzene sulfonamide was prepared by mixing 30.0 g of 4-chlorobenzene sulfonamide and 60.0 ml of chloroacetylchloride. The mixture was refluxed for 6 hours, allowed to cool, and stand at room temperature overnight. The crystalline product was removed by filtration, washed repeatedly with hexane, and dried. The product consisted of 32.5 g of reactant (m.p. 122°–124° C.). Structure was confirmed by IR and NMR.

The above-identified reactant (2.7 g or 0.01 mole), 25 ml of 1,3-dimethoxyethane, and 1.5 g (0.01 mole) of p-chlorothiophenol were stirred in an ice bath. 1.4 g (0.012 mole) of potassium t-butoxide was added to the mixture. The mixture was stirred for 15 minutes at room temperature and refluxed for 2 hours. Following cooling it was poured on water and extracted with methylene chloride. The organic layer was separated, water washed, dried over magnesium sulfate and filtered. The solvent was evaporated yielding 3.3 g of N-(4-chlorophenylthioacetyl) 4'-chlorobenzenesulfonamide ($n_D^{30}$ 1.5750). Structure was confirmed by IR and NMR.

EXAMPLE 3

(Compound No. 30)

Preparation of N-4'-chlorobenzoyl-4-chlorobenzene sulfonamide

4-Chlorobenzenesulfonamide (9.5 g or 0.05 mole) and 8.8 g (0.05 mole) of 4-chlorobenzoylchloride were added to 25 ml phosphorus oxychloride. The mixture was refluxed for 4 hours. After cooling it was poured into 300 ml of pentane and stirred in an ice bath for one hour. The product precipitate was recovered by filtration and dried yielding 10.9 g (m.p. 105°–109° C.). Structure was confirmed by IR and NMR.

EXAMPLE 4

(Compound No. 34)

Preparation of N-2-methoxypropionyl-O-toluene sulfonamide sodium salt

Sodium methoxide (0.02 mole) and 0.01 mole of N-2-chloropropionyl O-toluene sulfonamide (Compound 12) were stirred in 10 ml of methanol for ½ hour. The mixture was refluxed for 2½ hours cooled, stripped, and dried, yielding 2.4 g of product (m.p. 109°–114° C.). Structure was confirmed by IR and NMR.

Other metal salts, such as potassium, lithium, and aluminum, may be prepared by a similar reaction with a suitable reagent.

Other compounds typical of this invention are listed in Table I.

TABLE I

N—Acylsulfonamide Herbicidal Antidotes

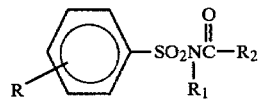

| Cmpd. No. | R | $R_1$ | $R_2$ | Chemical Name | Physical Constant |
|---|---|---|---|---|---|
| 1 | H | H | —CH$_3$ | N—benzenesulfonyl acetamide | m.p. 95–98° C. |
| 2 | H | H | —(CH$_2$)$_2$CH$_3$ | N—butyryl benzenesulfonamide | m.p. 85–87° C. |
| 3 | H | H | —CH(CH$_3$)$_2$ | N—isobutyryl benzenesulfonamide | m.p. 116–117° C. |
| 4 | —CH$_3$ | H | —C$_7$H$_{15}$ | N—tosyl caprylamide | m.p. 63–66° C. |
| 5 | —NHCOC$_2$H$_5$ | H | —CH$_3$ | N—(4'-ethoxycarbonylamidobenzenesulfonyl) acetamide | m.p. 96–100° C. |
| 6 | H | H | —CH$_2$Cl | N—benzenesulfonyl chloroacetamide | m.p. 85–88° C. |
| 7 | H | H | —CHCl$_2$ | N—benzenesulfonyl dichloroacetamide | m.p. 120–125° C. |
| 8 | H | H | —CHCl(CH$_3$) | N—2-chloropropionylbenzenesulfonamide | m.p. 110–113° C. |
| 9 | H | H | —CCl$_2$CH$_3$ | N—2,2-dichloropropionyl benzenesulfonamide | m.p. 60–70° C. |
| 10 | H | H | —CF$_3$ | N—trifluoroacetyl benzenesulfonamide | m.p. 126–131° C. |
| 11 | —CH$_3$ | H | —CH$_2$Cl | N—chloroacetyl-o-toluenesulfonamide | m.p. 108–110° C. |

TABLE I-continued

N—Acylsulfonamide Herbicidal Antidotes

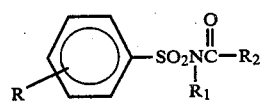

| Cmpd. No. | R | $R_1$ | $R_2$ | Chemical Name | Physical Constant |
|---|---|---|---|---|---|
| 12 | —CH₃ | H | —CHCl(CH₃) | N—2-chloropropionyl-o-toluene-sulfonamide | m.p. 99–101° C. |
| 13 | —CH₃ | H | —CHCl(CH₃) | N—2-chloropropionyl-p-toluene-sulfonamide | m.p. 111–113° C. |
| 14 | Cl | H | —CH₂Cl | N—chloroacetyl-p-chlorobenzene-sulfonamide | m.p. 122–124° C. |
| 15 | Cl | H | —CHCl(CH₃) | N—2-chloropropionyl-4′-chloro-benzenesulfonamide | m.p. 124–126° C. |
| 16 | Cl | H | —CH=CH₂ | N—acryloyl 4-chlorobenzene-sulfonamide | semi-solid |
| 17 | Cl | H | —CCl=CCl₂ | N—trichloroacryloyl 4-chloro-benzenesulfonamide | semi-solid |
| 18 | Cl | H | —CH₂C(O)CH₃ | N—acetoacetyl-4-chlorobenzene sulfonamide | m.p. |
| 19 | —NHC(O)CH₃ | H | —CH₃ | N,N′—diacetylsulfanilamide | m.p. 267° C. |
| 20 | Cl | H | —CH₂OCH₃ | N—methoxyacetyl-4-chloro-benzenesulfonamide | m.p. 57–59° C. |
| 21 | H | H | —COC(O)C₂H₅ | N—ethyloxalyl benzenesulfon-amide | $n_D^{30}$ 1.490 |
| 22 | —CH₃ | H | —COC(O)C₂H₅ | N—ethyloxalyl-o-toluene sulfonamide | m.p. 76–79° C. |
| 23 | Cl | H | —COC(O)C₂H₅ | N—ethyloxalyl-p-chlorobenzene sulfonamide | m.p. 67–70° C. |
| 24 | Cl | H | —CH₂SC₂H₅ | N—ethylthioacetyl-4-chloro-benzenesulfonamide | $n_D^{30}$ no line |
| 25 | Cl | H | —CH₂SP(S)(OC₂H₅)₂ | N—(2-O,O-diethylphosphorodi-thioylacetyl)-4-chlorobenzene-sulfonamide | m.p. 65–85° C. |
| 26 | Cl | H | —CH₂S—C₆H₄—Cl | N—(4-chlorophenylthioacetyl)-4′-chlorobenzenesulfonamide | $n_D^{30}$ 1.5750 |
| 27 | Cl | H | —CH₂SCH₂—C₆H₃Cl₂ | N—(4-chlorobenzenesulfonyl)-3′,4′-dichlorobenzylmercapto acetamide | semi-solid |
| 28 | Cl | H | —C₆H₅ | N—benzoyl-4-chlorobenzene sulfonamide | semi-solid |
| 29 | Cl | H | —C₆H₄Cl (2-Cl) | N—2-chlorobenzoyl-4′-chloro-benzenesulfonamide | m.p. 98–100° C. |
| 30 | Cl | H | —C₆H₄—Cl (4-Cl) | N—4′-chlorobenzoyl-4-chloro-benzenesulfonamide | m.p. 100–104° C. |

TABLE I-continued
N—Acylsulfonamide Herbicidal Antidotes

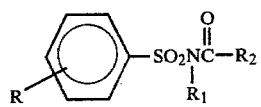

| Cmpd. No. | R | $R_1$ | $R_2$ | Chemical Name | Physical Constant |
|---|---|---|---|---|---|
| 31 | H | H | (2-fluorophenyl) | N—(2-fluorobenzoyl) benzene sulfonamide | m.p. 90–93° C. |
| 32 | Cl | H | —CNHSO$_2$—(4-Cl-phenyl) | N,N'—bis(4-chlorobenzenesulfonyl) oxamide | m.p. 259–262° C. |
| 33 | H | H | —(CH$_2$)$_2$CNHSO$_2$—(phenyl) | N,N'—bis(benzenesulfonyl) succinamide | m.p. 242–243° C. |
| 34 | —CH$_3$ | Na | —CHOCH$_3$ (with CH$_3$) | N—2-methoxypropionyl-o-toluene sulfonamide | m.p. 109–114° C. |
| 35 | —CH$_3$ | Na | —CHOC$_2$H$_5$ (with CH$_3$) | N—2-ethoxypropionyl-o-toluene sulfonamide | m.p. 105–110° C. |
| 36 | Cl | Na | —CH$_2$OC$_2$H$_5$ | N—ethoxyacetyl-p-chlorobenzene sulfonamide | m.p. 210–218° C. |
| 37 | Cl | Na | —CH$_2$OC$_3$H$_7$—n | N—n-propoxyacetyl-p-chloro-benzenesulfonamide | m.p. 186–196° C. |
| 38 | Cl | Na | —CH$_2$OC$_3$H$_7$—i | N—isopropoxyacetyl-p-chloro-benzenesulfonamide | m.p. 222–231° C. |
| 39 | Cl | Na | —CH$_2$OC$_4$H$_9$—n | N—n-butoxyacetyl-p-chloro-benzenesulfonamide | semi-solid |
| 40 | Cl | Na | —CH$_2$OC$_4$H$_9$—i | N—iso-butoxyacetyl-p-chloro benzenesulfonamide | m.p. 300° C. |
| 41 | Cl | Na | —CH$_2$OC$_4$H$_9$—sec | N—sec-butoxyacetyl-p-chloro-benzenesulfonamide | m.p. 179–186° C. |
| 42 | Cl | H | (2,6-dioxotetrahydrothiopyran-3-yl) | 2-(4'-chlorobenzenesulfonyl-amidocarbonyl)-1,3-cyclohexane-dione | m.p. 153–160° C. |
| 43 | Cl | H | (1,3-dimethylbarbituryl) | 1,3-dimethyl-4-(4'-chloro-benzenesulfonylamidocarbonyl)-barbituric acid | m.p. 172–175° C. |
| 44 | H | —C(CH$_2$)$_2$— | | N—benzenesulfonyl succinimide | m.p. 120–122° C. |
| 45 | H | (4,5-dichlorophthaloyl) | | N—benzenesulfonyl-4,5-dichloro-phthalimide | m.p. 152–160° C. |
| 46 | CH$_3$ | (phthaloyl) | | N—o-toluenesulfonyl phthalimide | m.p. 121–126° C. |
| 47 | CH$_3$ | (phthaloyl) | | N—p-toluenesulfonyl phthalimide | m.p. 230–234° C. |

TABLE I-continued
N—Acylsulfonamide Herbicidal Antidotes

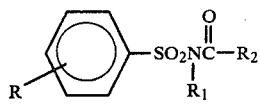

| Cmpd. No. | R | R₁ | R₂ | Chemical Name | Physical Constant |
|---|---|---|---|---|---|
| 48 | $CH_3$ | | (acetyl) 4,5-dichlorophenyl | N—o-toluenesulfonyl-4,5-dichlorophthalimide | m.p. 105–109° C. |
| 49 | $CH_3$ | | (acetyl) 4,5-dichlorophenyl | N—p-toluenesulfonyl-4,5-dichloro phthalimide | m.p. 174–182° C. |
| 50 | Cl | | (acetyl) phenyl | N—p-chlorobenzenesulfonyl phthalimide | m.p. 161–165° C. |
| 51 | Cl | | (acetyl) 4,5-dichlorophenyl | N—p-chlorobenzenesulfonyl-4,5-dichloro phthalimide | m.p. 192–196° C. |

Testing

Stock solutions of the herbicides were prepared by diluting the requisite amount of each herbicide in water. The solution concentrations and application rates and times are summarized in Table II.

TABLE II

| | Herbicide Stock Solutions | | | |
|---|---|---|---|---|
| | Concentration | | Application | |
| Herbicide Name | Herbicide (mg) | Water (ml) | ml/flat | lb/acre |
| VERNAM ® S—propyl N,N—dipropyl thiocarbamate | 390 | 400 | 5 | 1.00 |
| | 625 | 500 | 5 | 1.25 |
| | 672 | 400 | 5 | 1.70 |
| | 390 | 200 | 5 | 2.00 |
| | 2438 | 500 | 5 | 5.00 |
| | 2340 | 400 | 5 | 6.00 |
| | 2048 | 300 | 5 | 7.00 |
| RO-NEET ® S—ethyl N—ethyl N—cyclohexyl thiocarbamate | 780 | 250 | 5 | 3.00 |
| LASSO ® 2-chloro-2',6'-diethyl-N—(methoxymethyl) acetanilide | 3750 | 400 | linear spray | 3.00 |

Stock solutions of each antidote compound were prepared at the desired concentrations by diluting the requisite amounts of each antidote in acetone. The concentrations and rates for each method of application are summarized in Table III.

TABLE III

| Antidote Stock Solutions | | | | |
|---|---|---|---|---|
| Antidote: N—acylsulfonamide | | | | |
| Concentration | | Application | | |
| Antidote (mg) | Acetone (ml) | ml/flat | lb/acre | Method* |
| 95 | 15 | 0.30 | 1.00 | IF |
| 95 | 15 | 1.50 | 5.00 | IF |
| 40 | 25 | 1.25 | 0.50 | PPI |
| 40 | 25 | 2.50 | 1.00 | PPI |
| 40 | 25 | 5.00 | 2.00 | PPI |
| 40 | 10 | 5.00 | 5.00 | PPI |

*IF = In-furrow surface application.
PPI = Pre-plant incorporation of herbicide and antidote as a tank mix.

All of the soil used in the tests described herein was loamy sand soil treated with 50 parts per million (ppm) each of cis-N[(trichloromethyl)-thio]-4-cyclohexene-1,2-dicarboximide, a fungicide sold as Captan ®, and an 18-18-18 fertilizer, which contains 18% by weight equivalent each of nitrogen, phosphorus pentoxide, and potassium oxide.

The thiocarbamate herbicides were applied to the soil by pre-plant incorporation. The acetanilide stock solution was sprayed on the seeded flats on a linear spray table calibrated to deliver the equivalent of 80 gallons per acre (74.96 liters per hectare).

For in-furrow (IF) antidote applications, a one pint (473 cubic centimeters) sample of soil from each planting flat was removed and retained. After leveling and furrowing the soil, seeds of the crop or weed species were planted ½ inch (1.27 centimeter) deep. Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

For the pre-plant incorporation method the herbicide and the antidote of each test group were incorporated into the soil as a tank mix using a five gallon rotary mixer.

All flats were placed on greenhouse benches where temperature was maintained between 70° and 90° F. The flats were watered by sprinkling as needed to assure good plant growth.

Control flats contained crops treated with herbicides only at the various rates and methods of application.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were milo, wheat, cotton, rice, barley, corn and soybeans. Those compounds which showed substantial crop injury reduction were further tested at reduced rates. The herbicides and antidote compositions were then screened on at least two weed species. The weed species tested for control included watergrass (*Echinochloa crusgalli*), foxtail (*Setaria viridis*), wild oat (*Avena fatua*), Johnsongrass (*Sorghum halepense*), shattercane (*Sorghum bicolor*), and crabgrass (*Digitaria sp.*)

KEY TO TABLES IV AND V

Antidotes

Compound numbers in these tables correspond to the numbers and their chemical description in Table I.

Application:
- IF—In-furrow surface
- PPI—Pre-plant incorporation of herbicide and antidote as a tank mix

Herbicides

VERNAM®=S-propyl N,N-dipropylthiocarbamate as described in commonly assigned and expired U.S. Pat. No. 2,913,324

RONEET®=S-ethyl N-ethyl-N-cyclohexylthiocarbamate, as described in commonly assigned U.S. Pat. No. 3,185,720

LASSO®=2-chloro-2',6'-diethyl-N-(methoxymethyl) acetanilide as described in U.S. Pat. No. 3,442,945

Rates:
All rates are shown in pounds per acre.

Injury Ratings:
- U=Antidotally untreated; % Injury 4 weeks after herbicide application.
- T=Antidotally treated; % Injury 4 weeks after treatment with herbicide plus antidote compound
- —=Indicates no change

TABLE IV

Effectiveness of N—Acylsulfonamide Herbicidal Antidotes

| Cmpd. No. | Appli- cation Rate | Time | Herbicide Name | Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
| 1 | 5.00 | IF | VERNAM | 1.00 | 95 | — | 75 | 40 | 70 | 40 | 95 | — | 50 | 30 | | | | |
| | 5.00 | IF | VERNAM | 6.00 | | | | | | | | | | | 90 | — | 60 | — |
| | 1.00 | IF | VERNAM | 1.00 | | | 100 | — | | | | | 75 | — | | | | |
| | 5.00 | IF | VERNAM | 1.00 | | | 100 | 80 | | | | | 75 | — | | | | |
| | 5.00 | IF | LASSO | 3.00 | 98 | 75 | 70 | — | | | 99 | 95 | | | | | | |
| 2 | 5.00 | IF | VERNAM | 1.00 | 95 | 50 | 90 | 60 | 50 | — | 100 | — | 60 | — | | | | |
| | 5.00 | IF | VERNAM | 6.00 | | | | | | | | | | | 95 | — | 50 | 20 |
| | 1.00 | IF | VERNAM | 6.00 | | | | | | | | | | | | | 40 | — |
| | 5.00 | IF | VERNAM | 6.00 | | | | | | | | | | | | | 40 | 10 |
| | 5.00 | IF | LASSO | 3.00 | 98 | 90 | 70 | — | | | 99 | 95 | | | | | | |
| 3 | 5.00 | IF | VERNAM | 1.00 | 95 | 60 | 90 | — | 50 | 30 | 100 | — | 60 | — | | | | |
| | 5.00 | IF | VERNAM | 6.00 | | | | | | | | | | | 95 | — | 50 | 70 |
| | 1.00 | IF | VERNAM | 2.00 | | | | | 65 | 30 | | | | | | | | |
| | 5.00 | IF | VERNAM | 2.00 | | | | | 65 | 70 | | | | | | | | |
| 4 | 5.00 | IF | VERNAM | 1.00 | 95 | — | 75 | — | 70 | 55 | 95 | — | 50 | — | | | | |
| | 5.00 | IF | VERNAM | 6.00 | | | | | | | | | | | 90 | — | 60 | 70 |
| 5 | 5.00 | IF | VERNAM | 1.25 | 100 | — | 100 | — | 50 | 40 | 100 | 70 | 90 | — | | | | |
| | 5.00 | IF | VERNAM | 6.00 | | | | | | | | | | | 90 | — | 70 | 80 |
| | 1.00 | PPI | VERNAM | 5.00 | | | | | | | | | | | | | 60 | 50 |
| | 5.00 | PPI | VERNAM | 5.00 | | | | | | | | | | | | | 60 | 50 |
| 6 | 5.00 | IF | VERNAM | 1.00 | 95 | — | 75 | 60 | 70 | 40 | 95 | — | 50 | — | | | | |
| | 5.00 | IF | VERNAM | 6.00 | | | | | | | | | | | 90 | — | 60 | 40 |
| | 1.00 | IF | VERNAM | 5.00 | | | | | | | | | | | | | 40 | — |
| | 5.00 | IF | VERNAM | 5.00 | | | | | | | | | | | | | 40 | — |
| 7 | 5.00 | IF | VERNAM | 1.00 | 95 | — | 75 | 40 | 70 | 50 | 95 | — | 50 | 30 | | | | |
| | 5.00 | IF | VERNAM | 6.00 | | | | | | | | | | | 90 | — | 60 | 70 |
| | 1.00 | IF | VERNAM | 1.00 | | | 100 | — | | | | | 75 | — | | | | |
| | 5.00 | IF | VERNAM | 1.00 | | | 100 | — | | | | | 75 | — | | | | |
| | 5.00 | IF | LASSO | 3.00 | 98 | — | 70 | — | | | 99 | — | | | | | | |
| 8 | 5.00 | IF | VERNAM | 1.25 | 100 | — | 90 | 80 | 60 | — | 95 | — | 85 | — | | | | |
| | 5.00 | IF | VERNAM | 6.00 | | | | | | | | | | | 90 | — | 65 | 40 |
| | 1.00 | IF | VERNAM | 6.00 | | | | | | | | | | | | | 50 | 40 |
| | 5.00 | IF | VERNAM | 6.00 | | | | | | | | | | | | | 50 | 40 |
| | 1.00 | IF | VERNAM | 6.00 | | | | | | | | | | | | | 60 | 30 |
| | 5.00 | IF | VERNAM | 6.00 | | | | | | | | | | | | | 60 | — |
| | 0.50 | PPI | VERNAM | 6.00 | | | | | | | | | | | | | 65 | — |
| | 2.00 | PPI | VERNAM | 6.00 | | | | | | | | | | | | | 65 | 40 |
| 9 | 5.00 | IF | VERNAM | 1.00 | 100 | — | 85 | 100 | 50 | 80 | 95 | 100 | 55 | 100 | | | | |
| | 5.00 | IF | VERNAM | 6.00 | | | | | | | | | | | 95 | — | 60 | — |
| 10 | 5.00 | IF | VERNAM | 1.00 | 85 | — | 70 | — | 50 | — | 70 | 95 | 55 | — | | | | |
| | 5.00 | IF | VERNAM | 6.00 | | | | | | | | | | | 90 | — | 55 | — |
| | 0.50 | PPI | VERNAM | 1.00 | | | 95 | — | | | | | | | | | | |

TABLE IV-continued
Effectiveness of N—Acylsulfonamide Herbicidal Antidotes

| Cmpd. No. | Appli-cation Rate | Time | Herbicide Name | Rate | Milo U | T | Wheat U | T | Cotton U | T | Rice U | T | Barley U | T | Corn U | T | Soybean U | T |
|---|---|---|---|---|---|---|---|---|---|---|---|---|---|---|---|---|---|---|
| | 1.00 | PPI | VERNAM | 1.00 | | | 95 | — | | | | | | | | | | |
| | 5.00 | PPI | VERNAM | 1.00 | | | 95 | — | | | | | | | | | | |
| 11 | 5.00 | IF | VERNAM | 1.25 | 100 | 80 | 90 | 80 | 60 | — | 95 | 85 | 85 | — | | | | |
| | 5.00 | IF | VERNAM | 6.00 | | | | | | | | | | | 90 | — | 65 | 40 |
| | 1.00 | IF | VERNAM | 6.00 | | | | | | | | | | | | | 50 | — |
| | 5.00 | IF | VERNAM | 6.00 | | | | | | | | | | | | | 50 | — |
| | 1.00 | IF | VERNAM | 6.00 | | | | | | | | | | | | | 60 | 75 |
| | 5.00 | IF | VERNAM | 6.00 | | | | | | | | | | | | | 60 | 50 |
| | 0.50 | PPI | VERNAM | 6.00 | | | | | | | | | | | | | 65 | — |
| | 2.00 | PPI | VERNAM | 6.00 | | | | | | | | | | | | | 65 | — |
| 12 | 5.00 | IF | VERNAM | 1.25 | 100 | — | 95 | — | 60 | — | 100 | — | 90 | 100 | | | | |
| | 5.00 | IF | VERNAM | 6.00 | | | | | | | | | | | 85 | 70 | 70 | 30 |
| | 1.00 | IF | VERNAM | 5.00 | | | | | | | | | | | | | 60 | — |
| | 5.00 | IF | VERNAM | 5.00 | | | | | | | | | | | | | 60 | 10 |
| | 1.00 | IF | VERNAM | 6.00 | | | | | | | | | | | | | 60 | 30 |
| | 5.00 | IF | VERNAM | 6.00 | | | | | | | | | | | | | 60 | 30 |
| | 1.00 | PPI | VERNAM | 1.25 | | | | | | | | | 90 | — | | | | |
| | 2.00 | PPI | VERNAM | 1.25 | | | | | | | | | 90 | — | | | | |
| | 5.00 | PPI | VERNAM | 1.25 | | | | | | | | | 90 | — | | | | |
| | 0.50 | PPI | VERNAM | 6.00 | | | | | | | | | | | | | 65 | 50 |
| | 2.00 | PPI | VERNAM | 6.00 | | | | | | | | | | | | | 65 | 35 |
| 13 | 5.00 | IF | VERNAM | 1.25 | 100 | — | 90 | 70 | 60 | — | 95 | 80 | 85 | — | | | | |
| | 5.00 | IF | VERNAM | 6.00 | | | | | | | | | | | 90 | — | 65 | 40 |
| | 1.00 | IF | VERNAM | 6.00 | | | | | | | | | | | | | 50 | 40 |
| | 5.00 | IF | VERNAM | 6.00 | | | | | | | | | | | | | 50 | — |
| | 1.00 | IF | VERNAM | 6.00 | | | | | | | | | | | | | 60 | — |
| | 5.00 | IF | VERNAM | 6.00 | | | | | | | | | | | | | 60 | 40 |
| | 0.50 | PPI | VERNAM | 6.00 | | | | | | | | | | | | | 65 | — |
| | 2.00 | PPI | VERNAM | 6.00 | | | | | | | | | | | | | 65 | — |
| 14 | 5.00 | IF | VERNAM | 1.00 | 95 | 70 | 90 | 70 | 50 | 20 | 100 | — | 60 | 30 | | | | |
| | 5.00 | IF | VERNAM | 6.00 | | | | | | | | | | | 95 | — | 50 | — |
| | 1.00 | IF | VERNAM | 1.50 | | | | | | | | | 95 | — | | | | |
| | 5.00 | IF | VERNAM | 1.50 | | | | | | | | | 95 | — | | | | |
| | 1.00 | IF | VERNAM | 2.00 | | | | | 65 | 20 | | | | | | | | |
| | 5.00 | IF | VERNAM | 2.00 | | | | | 65 | — | | | | | | | | |
| | 1.00 | PPI | VERNAM | 1.25 | | | | | | | | | 90 | — | | | | |
| | 2.00 | PPI | VERNAM | 1.25 | | | | | | | | | 90 | — | | | | |
| | 5.00 | PPI | VERNAM | 1.25 | | | | | | | | | 90 | 80 | | | | |
| 15 | 5.00 | IF | VERNAM | 1.00 | 100 | — | 85 | — | 50 | — | 95 | 70 | 55 | 30 | | | | |
| | 5.00 | IF | VERNAM | 6.00 | | | | | | | | | | | 95 | — | 60 | 30 |
| | 1.00 | IF | VERNAM | 1.70 | | | | | | | | | 75 | — | | | | |
| | 5.00 | IF | VERNAM | 1.70 | | | | | | | | | 75 | — | | | | |
| | 1.00 | IF | VERNAM | 6.00 | | | | | | | | | | | | | 50 | 10 |
| | 5.00 | IF | VERNAM | 6.00 | | | | | | | | | | | | | 50 | 30 |
| | 0.50 | PPI | VERNAM | 7.00 | | | | | | | | | | | | | 50 | 40 |
| | 1.00 | PPI | VERNAM | 7.00 | | | | | | | | | | | | | 50 | 30 |
| | 2.00 | PPI | VERNAM | 7.00 | | | | | | | | | | | | | 50 | 20 |
| 16 | 5.00 | IF | VERNAM | 1.00 | 100 | — | 85 | — | 50 | 40 | 95 | — | 55 | — | | | | |
| | 5.00 | IF | VERNAM | 6.00 | | | | | | | | | | | 95 | — | 60 | — |
| 17 | 5.00 | IF | VERNAM | 1.00 | 100 | — | 85 | 100 | 50 | 40 | 95 | 100 | 55 | 80 | | | | |
| | 5.00 | IF | VERNAM | 6.00 | | | | | | | | | | | 95 | 80 | 60 | 50 |
| | 0.50 | PPI | VERNAM | 1.00 | | | 95 | — | | | | | | | | | | |
| | 1.00 | PPI | VERNAM | 1.00 | | | 95 | — | | | | | | | | | | |
| | 5.00 | PPI | VERNAM | 1.00 | | | 95 | — | | | | | | | | | | |
| | 1.00 | PPI | VERNAM | 1.25 | | | | | | | | | 90 | — | | | | |
| | 2.00 | PPI | VERNAM | 1.25 | | | | | | | | | 90 | — | | | | |
| | 5.00 | PPI | VERNAM | 1.25 | | | | | | | | | 90 | — | | | | |
| 18 | 5.00 | IF | VERNAM | 1.00 | 100 | — | 85 | — | 50 | 40 | 95 | — | 55 | — | | | | |
| | 5.00 | IF | VERNAM | 6.00 | | | | | | | | | | | 95 | — | 60 | 30 |
| | 1.00 | IF | VERNAM | 6.00 | | | | | | | | | | | | | 50 | 40 |
| | 5.00 | IF | VERNAM | 6.00 | | | | | | | | | | | | | 50 | 0 |
| | 5.00 | IF | LASSO | 3.00 | 98 | 95 | 70 | — | | | 99 | 95 | | | | | | |
| 19 | 5.00 | IF | VERNAM | 1.00 | 85 | — | 70 | 60 | 50 | — | 70 | 60 | 55 | — | | | | |
| | 5.00 | IF | VERNAM | 6.00 | | | | | | | | | | | 90 | — | 55 | — |
| 20 | 5.00 | IF | VERNAM | 1.25 | 100 | — | 95 | 80 | 50 | — | 95 | 80 | 70 | — | | | | |
| | 5.00 | IF | VERNAM | 6.00 | | | | | | | | | | | 95 | — | 50 | 20 |
| | 1.00 | IF | VERNAM | 6.00 | | | | | | | | | | | | | 65 | — |
| | 5.00 | IF | VERNAM | 6.00 | | | | | | | | | | | | | 65 | — |
| 21 | 5.00 | IF | VERNAM | 1.00 | 95 | — | 75 | — | 70 | — | 95 | — | 50 | — | | | | |
| | 5.00 | IF | VERNAM | 6.00 | | | | | | | | | | | 90 | — | 60 | 40 |
| | 1.00 | IF | VERNAM | 6.00 | | | | | | | | | | | | | 40 | 30 |
| | 5.00 | IF | VERNAM | 6.00 | | | | | | | | | | | | | 40 | — |
| | 0.50 | PPI | VERNAM | 6.00 | | | | | | | | | | | | | 60 | — |
| | 1.00 | PPI | VERNAM | 6.00 | | | | | | | | | | | | | 60 | 50 |
| 22 | 5.00 | IF | VERNAM | 1.25 | 100 | — | 95 | — | 60 | — | 100 | — | 90 | — | | | | |
| | 5.00 | IF | VERNAM | 6.00 | | | | | | | | | | | 85 | — | 70 | — |

TABLE IV-continued

Effectiveness of N—Acylsulfonamide Herbicidal Antidotes

| Cmpd. No. | Appli-cation Rate | Time | Herbicide Name | Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
| 23 | 5.00 | IF | VERNAM | 1.25 | 100 | — | 95 | — | 60 | — | 100 | — | 90 | 60 | | | | |
|    | 5.00 | IF | VERNAM | 6.00 | | | | | | | | | | | 85 | — | 70 | — |
| 24 | 5.00 | IF | VERNAM | 1.25 | 100 | 70 | 95 | — | 50 | 30 | 95 | — | 70 | — | | | | |
|    | 5.00 | IF | VERNAM | 6.00 | | | | | | | | | | | 95 | — | 50 | — |
| 25 | 5.00 | IF | VERNAM | 1.25 | 100 | 80 | 95 | — | 50 | 30 | 95 | — | 70 | — | | | | |
|    | 5.00 | IF | VERNAM | 6.00 | | | | | | | | | | | 95 | — | 50 | — |
| 26 | 5.00 | IF | VERNAM | 1.25 | 100 | 40 | 95 | — | 50 | 30 | 95 | 60 | 70 | — | | | | |
|    | 5.00 | IF | VERNAM | 6.00 | | | | | | | | | | | 95 | — | 50 | — |
|    | 1.00 | IF | RONEET | 3.00 | 75 | 60 | | | | | | | | | | | | |
|    | 5.00 | IF | RONEET | 3.00 | 75 | 10 | | | | | | | | | | | | |
|    | 5.00 | IF | LASSO  | 3.00 | 98 | 60 | 70 | 60 | | | 99 | — | | | | | | |
| 27 | 5.00 | IF | VERNAM | 1.25 | 100 | — | 95 | — | 50 | — | 95 | — | 70 | 100 | | | | |
|    | 5.00 | IF | VERNAM | 6.00 | | | | | | | | | | | 95 | — | 50 | — |
|    | 1.00 | PPI | VERNAM | 1.25 | | | | | | | | | 70 | — | | | | |
|    | 5.00 | PPI | VERNAM | 1.25 | | | | | | | | | 70 | — | | | | |
| 28 | 5.00 | IF | VERNAM | 1.00 | 100 | — | 85 | — | 50 | — | 95 | — | 55 | — | | | | |
|    | 5.00 | IF | VERNAM | 6.00 | | | | | | | | | | | 95 | — | 60 | 40 |
| 29 | 5.00 | IF | VERNAM | 1.00 | 100 | — | 85 | — | 50 | — | 95 | — | 55 | — | | | | |
|    | 5.00 | IF | VERNAM | 6.00 | | | | | | | | | | | 95 | — | 60 | 30 |
|    | 1.00 | IF | VERNAM | 6.00 | | | | | | | | | | | | | 50 | 10 |
|    | 5.00 | IF | VERNAM | 6.00 | | | | | | | | | | | | | 50 | — |
|    | 0.50 | PPI | VERNAM | 7.00 | | | | | | | | | | | | | 50 | 40 |
|    | 1.00 | PPI | VERNAM | 7.00 | | | | | | | | | | | | | 50 | 40 |
|    | 2.00 | PPI | VERNAM | 7.00 | | | | | | | | | | | | | 50 | 40 |
| 30 | 5.00 | IF | VERNAM | 1.00 | 95 | — | 90 | — | 60 | — | 95 | 60 | 70 | — | | | | |
|    | 5.00 | IF | VERNAM | 6.00 | | | | | | | | | | | 90 | — | 60 | 20 |
|    | 1.00 | IF | VERNAM | 6.00 | | | | | | | | | | | | | 45 | 20 |
|    | 5.00 | IF | VERNAM | 6.00 | | | | | | | | | | | | | 45 | 20 |
|    | 1.00 | IF | VERNAM | 6.00 | | | | | | | | | | | | | 40 | 10 |
|    | 5.00 | IF | VERNAM | 6.00 | | | | | | | | | | | | | 40 | 0 |
|    | 0.50 | PPI | VERNAM | 6.00 | | | | | | | | | | | | | 50 | 40 |
|    | 1.00 | PPI | VERNAM | 6.00 | | | | | | | | | | | | | 50 | 40 |
|    | 2.00 | PPI | VERNAM | 6.00 | | | | | | | | | | | | | 50 | 30 |
| 31 | 5.00 | IF | VERNAM | 1.00 | 100 | — | 85 | — | 50 | — | 95 | — | 55 | — | | | | |
|    | 5.00 | IF | VERNAM | 6.00 | | | | | | | | | | | 95 | — | 60 | 50 |
| 32 | 5.00 | IF | VERNAM | 1.00 | 100 | — | 85 | — | 50 | — | 95 | — | 55 | — | | | | |
|    | 5.00 | IF | VERNAM | 6.00 | | | | | | | | | | | 95 | — | 60 | — |
| 33 | 5.00 | IF | VERNAM | 1.00 | 95 | — | 75 | 90 | 70 | 30 | 95 | — | 50 | — | | | | |
|    | 5.00 | IF | VERNAM | 6.00 | | | | | | | | | | | 90 | — | 60 | — |
| 34 | 5.00 | IF | VERNAM | 1.25 | 100 | — | 90 | 85 | 60 | — | 95 | — | 85 | — | | | | |
|    | 5.00 | IF | VERNAM | 6.00 | | | | | | | | | | | 90 | — | 65 | 20 |
|    | 1.00 | IF | VERNAM | 6.00 | | | | | | | | | | | | | 50 | 30 |
|    | 5.00 | IF | VERNAM | 6.00 | | | | | | | | | | | | | 50 | 20 |
|    | 1.00 | IF | VERNAM | 6.00 | | | | | | | | | | | | | 60 | 30 |
|    | 5.00 | IF | VERNAM | 6.00 | | | | | | | | | | | | | 60 | 30 |
|    | 0.50 | PPI | VERNAM | 6.00 | | | | | | | | | | | | | 65 | — |
|    | 2.00 | PPI | VERNAM | 6.00 | | | | | | | | | | | | | 65 | — |
| 35 | 5.00 | IF | VERNAM | 1.25 | 100 | 85 | 90 | — | 60 | — | 95 | — | 85 | — | | | | |
|    | 5.00 | IF | VERNAM | 6.00 | | | | | | | | | | | 90 | — | 65 | — |
| 36 | 5.00 | IF | VERNAM | 1.25 | 100 | 60 | 95 | — | 60 | — | 100 | — | 90 | — | | | | |
|    | 5.00 | IF | VERNAM | 6.00 | | | | | | | | | | | 85 | — | 70 | — |
| 37 | 5.00 | IF | VERNAM | 1.25 | 100 | — | 90 | — | 60 | — | 95 | — | 85 | — | | | | |
|    | 5.00 | IF | VERNAM | 6.00 | | | | | | | | | | | 90 | — | 65 | — |
| 38 | 5.00 | IF | VERNAM | 1.25 | 100 | — | 95 | — | 60 | — | 100 | — | 90 | — | | | | |
|    | 5.00 | IF | VERNAM | 6.00 | | | | | | | | | | | 85 | — | 70 | — |
| 39 | 5.00 | IF | VERNAM | 1.25 | 100 | — | 90 | — | 60 | 50 | 95 | — | 85 | — | | | | |
|    | 5.00 | IF | VERNAM | 6.00 | | | | | | | | | | | 90 | — | 65 | — |
| 40 | 5.00 | IF | VERNAM | 1.25 | 100 | — | 90 | 80 | 60 | — | 95 | — | 85 | — | | | | |
|    | 5.00 | IF | VERNAM | 6.00 | | | | | | | | | | | 90 | — | 65 | — |
| 41 | 5.00 | IF | VERNAM | 1.25 | 100 | — | 90 | — | 60 | — | 95 | — | 85 | — | | | | |
|    | 5.00 | IF | VERNAM | 6.00 | | | | | | | | | | | 90 | — | 65 | — |
| 42 | 5.00 | IF | VERNAM | 1.00 | 95 | 70 | 90 | — | 50 | — | 100 | — | 100 | — | | | | |
|    | 5.00 | IF | VERNAM | 6.00 | | | | | | | | | | | 95 | — | 50 | 30 |
|    | 1.00 | IF | VERNAM | 6.00 | | | | | | | | | | | | | 40 | — |
|    | 5.00 | IF | VERNAM | 6.00 | | | | | | | | | | | | | 40 | 20 |
| 43 | 5.00 | IF | VERNAM | 1.00 | 95 | 80 | 90 | — | 50 | 40 | 100 | — | 60 | — | | | | |
|    | 5.00 | IF | VERNAM | 6.00 | | | | | | | | | | | 95 | — | 50 | 30 |
|    | 1.00 | IF | VERNAM | 6.00 | | | | | | | | | | | | | 40 | — |
|    | 5.00 | IF | VERNAM | 6.00 | | | | | | | | | | | | | 40 | 20 |
| 44 | 5.00 | IF | VERNAM | 1.00 | 100 | — | 85 | — | 50 | 100 | 95 | 100 | 55 | 30 | | | | |
|    | 5.00 | IF | VERNAM | 6.00 | | | | | | | | | | | 95 | — | 60 | 40 |
|    | 1.00 | IF | VERNAM | 1.70 | | | | | | | | | 75 | 40 | | | | |
|    | 5.00 | IF | VERNAM | 1.70 | | | | | | | | | 75 | 60 | | | | |
|    | 0.50 | PPI | VERNAM | 1.25 | | | | | | | | | 50 | — | | | | |
|    | 1.00 | PPI | VERNAM | 1.25 | | | | | | | | | 50 | — | | | | |
|    | 2.00 | PPI | VERNAM | 1.25 | | | | | | | | | 50 | — | | | | |

TABLE IV-continued

Effectiveness of N—Acylsulfonamide Herbicidal Antidotes

| Cmpd. No. | Application Rate | Time | Herbicide Name | Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
| 45 | 5.00 | IF | VERNAM | 1.25 | 100 | 85 | 100 | — | 50 | — | 100 | — | 90 | 100 | | | | |
|  | 5.00 | IF | VERNAM | 6.00 | | | | | | | | | | | 90 | — | 70 | 100 |
|  | 1.00 | PPI | VERNAM | 1.25 | | | | | | | | | 70 | — | | | | |
|  | 5.00 | PPI | VERNAM | 1.25 | | | | | | | | | 70 | — | | | | |
|  | 1.00 | PPI | VERNAM | 5.00 | | | | | | | | | | | | | 60 | 35 |
|  | 5.00 | PPI | VERNAM | 5.00 | | | | | | | | | | | | | 60 | 30 |
| 46 | 5.00 | IF | VERNAM | 1.25 | 100 | — | 100 | — | 50 | — | 100 | — | 90 | 80 | | | | |
|  | 5.00 | IF | VERNAM | 6.00 | | | | | | | | | | | 90 | — | 70 | — |
| 47 | 5.00 | IF | VERNAM | 1.25 | 100 | — | 100 | — | 50 | — | 100 | — | 90 | — | | | | |
|  | 5.00 | IF | VERNAM | 6.00 | | | | | | | | | | | 90 | — | 70 | — |
| 48 | 5.00 | IF | VERNAM | 1.25 | 100 | — | 100 | — | 50 | — | 100 | — | 90 | 70 | | | | |
|  | 5.00 | IF | VERNAM | 6.00 | | | | | | | | | | | 90 | — | 70 | — |
| 49 | 5.00 | IF | VERNAM | 1.25 | 100 | — | 100 | — | 50 | — | 100 | 85 | 90 | 70 | | | | |
|  | 5.00 | IF | VERNAM | 6.00 | | | | | | | | | | | 90 | — | 70 | — |
| 50 | 5.00 | IF | VERNAM | 1.25 | 100 | 80 | 100 | 80 | 50 | — | 100 | — | 90 | 70 | | | | |
|  | 5.00 | IF | VERNAM | 6.00 | | | | | | | | | | | 90 | — | 70 | 80 |
|  | 1.00 | PPI | VERNAM | 5.00 | | | | | | | | | | | | | 60 | 40 |
|  | 5.00 | PPI | VERNAM | 5.00 | | | | | | | | | | | | | 60 | — |
| 51 | 5.00 | IF | VERNAM | 1.25 | 100 | 85 | 100 | 80 | 50 | — | 100 | — | 90 | 70 | | | | |
|  | 5.00 | IF | VERNAM | 6.00 | | | | | | | | | | | 90 | — | 70 | — |

TABLE V

Herbicidal Effectiveness

| Antidote Cmpd. No. | Application Rate | Time | Herbicide Name | Rate | Watergrass U | Watergrass T | Foxtail U | Foxtail T | Wild oat U | Wild oat T | Johnsongrass U | Johnsongrass T | Shattercane U | Shattercane T | Crabgrass U | Crabgrass T |
|---|---|---|---|---|---|---|---|---|---|---|---|---|---|---|---|---|
| 1 | 1.00 | IF | VERNAM | 1.00 | 70 | — | | | 100 | — | | | | | | |
|  | 5.00 | IF | VERNAM | 1.00 | 70 | — | | | 100 | — | | | | | | |
| 2 | 1.00 | IF | VERNAM | 6.00 | 100 | — | 100 | — | | | | | | | | |
|  | 5.00 | IF | VERNAM | 6.00 | 100 | — | 100 | — | | | | | | | | |
| 3 | 1.00 | IF | VERNAM | 2.00 | 70 | — | 60 | — | | | | | | | | |
|  | 5.00 | IF | VERNAM | 2.00 | 70 | — | 60 | — | | | | | | | | |
| 5 | 1.00 | PPI | VERNAM | 5.00 | 95 | — | 95 | — | | | | | | | | |
|  | 5.00 | PPI | VERNAM | 5.00 | 95 | — | 95 | — | | | | | | | | |
| 6 | 1.00 | IF | VERNAM | 5.00 | 100 | — | 100 | — | | | | | | | | |
|  | 5.00 | IF | VERNAM | 5.00 | 100 | — | 100 | — | | | | | | | | |
| 8 | 1.00 | IF | VERNAM | 6.00 | 100 | — | | | | | 100 | — | | | | |
|  | 5.00 | IF | VERNAM | 6.00 | 100 | — | | | | | 100 | — | | | | |
|  | 1.00 | IF | VERNAM | 6.00 | 98 | — | 98 | — | | | | | | | | |
|  | 5.00 | IF | VERNAM | 6.00 | 98 | — | 98 | — | | | | | | | | |
|  | 0.50 | PPI | VERNAM | 6.00 | 98 | — | 100 | — | | | | | | | | |
|  | 2.00 | PPI | VERNAM | 6.00 | 98 | — | 100 | — | | | | | | | | |
| 10 | 0.50 | PPI | VERNAM | 1.00 | 95 | — | 95 | — | | | | | | | | |
|  | 1.00 | PPI | VERNAM | 1.00 | 95 | — | 95 | — | | | | | | | | |
|  | 5.00 | PPI | VERNAM | 1.00 | 95 | — | 95 | — | | | | | | | | |
| 11 | 1.00 | IF | VERNAM | 6.00 | 100 | — | | | | | 100 | — | | | | |
|  | 5.00 | IF | VERNAM | 6.00 | 100 | — | | | | | 100 | — | | | | |
|  | 1.00 | IF | VERNAM | 6.00 | 98 | — | 98 | — | | | | | | | | |
|  | 5.00 | IF | VERNAM | 6.00 | 98 | — | 98 | — | | | | | | | | |
|  | 0.50 | PPI | VERNAM | 6.00 | 98 | — | 100 | — | | | | | | | | |
|  | 2.00 | PPI | VERNAM | 6.00 | 98 | — | 100 | — | | | | | | | | |
| 12 | 1.00 | IF | VERNAM | 5.00 | 95 | — | 95 | — | | | | | | | | |
|  | 5.00 | IF | VERNAM | 5.00 | 95 | — | 95 | — | | | | | | | | |
|  | 1.00 | IF | VERNAM | 6.00 | 98 | — | 98 | — | | | | | | | | |
|  | 5.00 | IF | VERNAM | 6.00 | 98 | — | 98 | — | | | | | | | | |
|  | 1.00 | PPI | VERNAM | 1.25 | 97 | — | 97 | — | | | | | | | | |
|  | 2.00 | PPI | VERNAM | 1.25 | 97 | — | 97 | — | | | | | | | | |
|  | 5.00 | PPI | VERNAM | 1.25 | 97 | — | 97 | — | | | | | | | | |
|  | 0.50 | PPI | VERNAM | 6.00 | 98 | — | 100 | — | | | | | | | | |
|  | 2.00 | PPI | VERNAM | 6.00 | 98 | — | 100 | — | | | | | | | | |
| 13 | 1.00 | IF | VERNAM | 6.00 | 100 | — | | | | | 100 | — | | | | |
|  | 5.00 | IF | VERNAM | 6.00 | 100 | — | | | | | 100 | — | | | | |
|  | 1.00 | IF | VERNAM | 6.00 | 98 | — | 98 | — | | | | | | | | |
|  | 5.00 | IF | VERNAM | 6.00 | 98 | — | 98 | — | | | | | | | | |
|  | 0.50 | PPI | VERNAM | 6.00 | 98 | — | 100 | — | | | | | | | | |
|  | 2.00 | PPI | VERNAM | 6.00 | 98 | — | 100 | — | | | | | | | | |
| 14 | 1.00 | IF | VERNAM | 1.50 | | | 70 | — | 100 | — | | | | | | |
|  | 5.00 | IF | VERNAM | 1.50 | | | 70 | — | 100 | — | | | | | | |
|  | 1.00 | IF | VERNAM | 2.00 | 70 | — | 60 | — | | | | | | | | |
|  | 5.00 | IF | VERNAM | 2.00 | 70 | — | 60 | — | | | | | | | | |
|  | 1.00 | PPI | VERNAM | 1.25 | 97 | — | 97 | — | | | | | | | | |
|  | 2.00 | PPI | VERNAM | 1.25 | 97 | — | 97 | — | | | | | | | | |
|  | 5.00 | PPI | VERNAM | 1.25 | 97 | — | 97 | — | | | | | | | | |

TABLE V-continued

| Antidote | | | Herbicide | | Herbicidal Effectiveness % Weed Injury | | | | | | | | | | | | |
|---|---|---|---|---|---|---|---|---|---|---|---|---|---|---|---|---|---|
| Cmpd. No. | Application Rate | Time | Name | Rate | Watergrass U | T | Foxtail U | T | Wild oat U | T | Johnsongrass U | T | Shattercane U | T | Crabgrass U | T |
| 15 | 1.00 | IF | VERNAM | 1.70 | 60 | — | 60 | — | | | | | | | | |
|  | 5.00 | IF | VERNAM | 1.70 | 60 | — | 60 | — | | | | | | | | |
|  | 1.00 | IF | VERNAM | 6.00 | 100 | — | 100 | — | | | | | | | | |
|  | 5.00 | IF | VERNAM | 6.00 | 100 | — | 100 | — | | | | | | | | |
|  | 0.50 | PPI | VERNAM | 7.00 | 100 | — | 100 | — | | | | | | | | |
|  | 1.00 | PPI | VERNAM | 7.00 | 100 | — | 100 | — | | | | | | | | |
|  | 2.00 | PPI | VERNAM | 7.00 | 100 | — | 100 | — | | | | | | | | |
| 17 | 0.50 | PPI | VERNAM | 1.00 | 95 | — | 95 | — | | | | | | | | |
|  | 1.00 | PPI | VERNAM | 1.00 | 95 | — | 95 | — | | | | | | | | |
|  | 5.00 | PPI | VERNAM | 1.00 | 95 | — | 95 | — | | | | | | | | |
|  | 1.00 | PPI | VERNAM | 1.25 | 97 | — | 97 | — | | | | | | | | |
|  | 2.00 | PPI | VERNAM | 1.25 | 97 | — | 97 | — | | | | | | | | |
|  | 5.00 | PPI | VERNAM | 1.25 | 97 | — | 97 | — | | | | | | | | |
| 18 | 1.00 | IF | VERNAM | 6.00 | 100 | — | 100 | — | | | | | | | | |
|  | 5.00 | IF | VERNAM | 6.00 | 100 | — | 100 | 80 | | | | | | | | |
| 20 | 1.00 | IF | VERNAM | 6.00 | 100 | — | 100 | — | | | | | | | | |
|  | 5.00 | IF | VERNAM | 6.00 | 100 | — | 100 | — | | | | | | | | |
| 21 | 1.00 | IF | VERNAM | 6.00 | 100 | — | 100 | — | | | | | | | | |
|  | 5.00 | IF | VERNAM | 6.00 | 100 | — | 100 | — | | | | | | | | |
|  | 0.50 | PPI | VERNAM | 6.00 | 100 | — | 90 | — | | | | | | | | |
|  | 1.00 | PPI | VERNAM | 6.00 | 100 | — | 90 | — | | | | | | | | |
| 26 | 1.00 | IF | RONEET | 3.00 | | | 80 | — | | | | | 95 | — | | |
|  | 5.00 | IF | RONEET | 3.00 | | | 80 | — | | | | | 95 | — | | |
| 29 | 1.00 | IF | VERNAM | 6.00 | 100 | — | 100 | — | | | | | | | | |
|  | 5.00 | IF | VERNAM | 6.00 | 100 | — | 100 | — | | | | | | | | |
|  | 0.50 | PPI | VERNAM | 7.00 | 100 | — | 100 | — | | | | | | | | |
|  | 1.00 | PPI | VERNAM | 7.00 | 100 | — | 100 | — | | | | | | | | |
|  | 2.00 | PPI | VERNAM | 7.00 | 100 | — | 100 | — | | | | | | | | |
| 30 | 1.00 | IF | VERNAM | 6.00 | | | 100 | — | | | | | | | 95 | — |
|  | 5.00 | IF | VERNAM | 6.00 | 1 | — | 100 | — | | | | | | | 95 | — |
|  | 1.00 | IF | VERNAM | 6.00 | 100 | — | 100 | — | | | | | | | | |
|  | 5.00 | IF | VERNAM | 6.00 | 100 | — | 100 | — | | | | | | | | |
|  | 0.50 | PPI | VERNAM | 7.00 | 100 | — | 100 | — | | | | | | | | |
|  | 1.00 | PPI | VERNAM | 7.00 | 100 | — | 100 | — | | | | | | | | |
|  | 2.00 | PPI | VERNAM | 7.00 | 100 | — | 100 | — | | | | | | | | |
| 34 | 1.00 | IF | VERNAM | 6.00 | 100 | — | | | | | 100 | — | | | | |
|  | 5.00 | IF | VERNAM | 6.00 | 100 | — | | | | | 100 | — | | | | |
|  | 1.00 | IF | VERNAM | 6.00 | 98 | — | 98 | — | | | | | | | | |
|  | 5.00 | IF | VERNAM | 6.00 | 98 | — | 98 | — | | | | | | | | |
|  | 0.50 | PPI | VERNAM | 6.00 | 98 | — | 100 | — | | | | | | | | |
|  | 2.00 | PPI | VERNAM | 6.00 | 98 | — | 100 | — | | | | | | | | |
| 42 | 1.00 | IF | VERNAM | 6.00 | 100 | — | 100 | — | | | | | | | | |
|  | 5.00 | IF | VERNAM | 6.00 | 100 | — | 100 | — | | | | | | | | |
| 43 | 1.00 | IF | VERNAM | 6.00 | 100 | — | 100 | — | | | | | | | | |
|  | 5.00 | IF | VERNAM | 6.00 | 100 | — | 100 | — | | | | | | | | |
| 44 | 1.00 | IF | VERNAM | 1.70 | 60 | 20 | 60 | 50 | | | | | | | | |
|  | 5.00 | IF | VERNAM | 1.70 | 60 | 30 | 60 | — | | | | | | | | |
|  | 0.50 | PPI | VERNAM | 1.25 | 100 | — | | | 100 | — | | | | | | |
|  | 1.00 | PPI | VERNAM | 1.25 | 100 | — | | | 100 | — | | | | | | |
|  | 2.00 | PPI | VERNAM | 1.25 | 100 | — | | | 100 | — | | | | | | |
| 45 | 1.00 | PPI | VERNAM | 1.25 | | | 70 | — | 100 | — | | | | | | |
|  | 5.00 | PPI | VERNAM | 1.25 | | | 70 | — | 100 | — | | | | | | |
|  | 1.00 | PPI | VERNAM | 5.00 | 95 | — | 95 | — | | | | | | | | |
|  | 5.00 | PPI | VERNAM | 5.00 | 95 | — | 95 | — | | | | | | | | |
| 50 | 1.00 | PPI | VERNAM | 5.00 | 95 | — | 95 | — | | | | | | | | |
|  | 5.00 | PPI | VERNAM | 5.00 | 95 | — | 95 | — | | | | | | | | |

Test Results

The compositions of this invention show good antidotal activity for a variety of crops, especially soybeans. They were effective by either IF or PPI methods of application.

Formulations

The compounds and compositions can be formulated in the same manner in which herbicides are generally formulated. The object of the formulation is to apply the compounds and compositions to the loci where control is desired by a conventional method. The "loci" may include soil, seeds, seedlings, and vegetation.

Formulations will generally contain several additives. Among these are some inert ingredients and diluent carriers such as organic solvents, water, oil and water, water in oil emulsions, carriers of dusts and granules, and surface active wetting, dispersing, and emulsifying agents.

Fertilizers, e.g., ammonium nitrate, urea and superphosphate, may also be added.

Aids to rooting and growth, e.g., compost, manure, humus, sand, etc., may likewise be added.

The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and antistatic agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

What I claim:

1. A compound of the formula

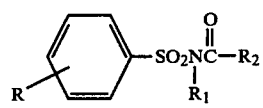

in which
R is methyl or chloro;
$R_1$ is selected from the group consisting of hydrogen and a metal ion;
$R_2$ is alkoxyalkyl having 2–5 carbon atoms.

2. A compound according to claim 1 in which R is chloro, $R_1$ is hydrogen, and $R_2$ is methoxymethyl.

3. A compound according to claim 1 in which R is methyl, $R_1$ is sodium ion, and $R_2$ is 1-methoxyethyl.

* * * * *